US008502152B1

(12) United States Patent
Hashmonay et al.

(10) Patent No.: US 8,502,152 B1
(45) Date of Patent: Aug. 6, 2013

(54) METHOD FOR OPEN PATH DETECTION OF AIR CONTAMINANTS

(71) Applicant: Atmosfir Optics Ltd, Ein Iron (IL)

(72) Inventors: Ram Hashmonay, Chapel Hill, NC (US); Robert Howard Kagann, Cumming, GA (US); Gilad Shpitzer, Ein Iron (IL); Yair Shpitzer, Jerusalem (IL); Michael James Chase, Raleigh, NC (US)

(73) Assignee: Atmosfir Optics Ltd., Ein Iron (IL)

( * ) Notice: Subject to any disclaimer, the term of this patent is extended or adjusted under 35 U.S.C. 154(b) by 0 days.

(21) Appl. No.: 13/745,808

(22) Filed: Jan. 20, 2013

(51) Int. Cl.
*G01N 21/35* (2006.01)
(52) U.S. Cl.
USPC .................................................. 250/339.12
(58) Field of Classification Search
USPC .................................................. 250/339.12
See application file for complete search history.

(56) References Cited

U.S. PATENT DOCUMENTS

| 5,807,750 | A | * | 9/1998 | Baum et al. | 436/164 |
| 5,827,942 | A | * | 10/1998 | Madsen et al. | 73/1.82 |
| 6,483,113 | B1 | * | 11/2002 | Sealy et al. | 250/339.08 |
| 6,542,242 | B1 | * | 4/2003 | Yost et al. | 356/450 |
| 7,229,833 | B1 | * | 6/2007 | Andersson | 436/73 |
| 7,501,629 | B2 | * | 3/2009 | Hashmonay | 250/339.08 |
| 2006/0246592 | A1 | * | 11/2006 | Hashmonay | 436/57 |
| 2007/0045542 | A1 | * | 3/2007 | Hashmonay | 250/339.12 |

* cited by examiner

*Primary Examiner* — David Porta
*Assistant Examiner* — Casey Bryant
(74) *Attorney, Agent, or Firm* — Soroker-Agmon; Daniel Schatz

(57) ABSTRACT

The subject matter discloses a method for detecting concentration of air contaminants, comprising obtaining an average sample single beam value, the average sample single beam value comprises a first set of single beam measurements obtained from a detector; obtaining an average background single beam value, the average background single beam value comprises a second set of single beam measurements obtained from the detector; comparing the average sample single beam value to the average background single beam value to determine the concentration of air contamination; continuously updating the averages upon detection of new single beam measurements; wherein the second set of single beam measurements comprises a plurality of single beam measurements that were detected by the detector prior to the detection of the single beam measurements included in the first set of single beam measurements. In some cases, the first set partially overlaps with the second set.

14 Claims, 4 Drawing Sheets

METHOD FOR OPEN PATH DETECTION OF AIR CONTAMINANTS

FIELD OF THE INVENTION

The subject matter relates generally to air contaminant detector and more specifically a method of detecting air contaminants using radiation intensity measurements.

BACKGROUND OF THE INVENTION

Open-Path spectroscopic analyzers are used to provide quantitative information on a chemical mixture of gases and aerosol that propagate from emission sources. Detailed information on the emissions can sometimes be obtained from the sources using multiple open-paths that may be scanned by a single Open-path spectrometer. Detection of the chemical mixture of gases and aerosol includes data acquisition of sample spectrum, data reduction and selection of a background spectrum. There are three data acquisition scenarios. The first discloses a series of electromagnetic spectra $S(\lambda)$ (intensity S vs. wavelength $\lambda$) acquired sequentially over a defined path length (extractive or open path). The second discloses a series of electromagnetic spectra acquired sequentially over a spatially adjacent direction. This can be achieved for example with passive infrared or passive ultraviolet spectrometer pointing to the sky or to a blocking mountain range. The third scenario discloses a series of electromagnetic spectra acquired sequentially over the same direction from a moving platform. Examples: solar occultation flux, mobile sky looking spectroscopy, and airborne down looking spectroscopy.

There are three steps of data reduction for the input spectrum (absorption, emission spectrum, or extinction with particle presence) into the quantification algorithm. The first is acquisition and data reduction of the single beam sample spectrum $S(\lambda)$ and the second step is the selection of the single beam background spectrum $S_0(\lambda)$. The transmission is the ratio $$\left(\frac{S}{S_0}\right)$$

used to determine absorbance, emission or extinction. In the third step, the transmission is used for generation of a double beam (DB) value and subsequently for determining the quantity of an air contaminant in a plume. The absorbance spectrum is defined as the negative logarithm of S divided by $S_0$, represented by the equation $$A = -\log_{10}\left(\frac{S}{S_0}\right).$$

Extinction is defined by the sum of absorption and scattering. The emission spectrum is defined as the logarithm of S divided by $S_0$, represented by the equation $$E = \log_{10}\left(\frac{S}{S_0}\right).$$

SUMMARY

It is an object of the subject matter to disclose a method for detecting concentration of air contaminants, comprising:

obtaining an average sample single beam value, the average Single Beam value comprises a first set of Single Beam measurements obtained from a detector. The Single Beam (SB) measurements are the radiation intensity signal at a specific wavelength;

obtaining an average background SB value, the average background SB value comprises a second set of SB measurements obtained from the detector;

comparing the average sample SB value to the average background SB value to determine the concentration of air contamination;

continuously updating the averages upon detection of new SB measurements;

wherein the second set of SB measurements comprises a plurality SB measurements at least a portion of which were acquired by the detector prior to the acquisition of the SB measurements included in the first set of SB measurements.

In some cases, each SB measurement of the plurality of SB measurements comprises an electromagnetic (EM) radiation measurement.

In some cases, the EM radiation measurement comprises an average of a plurality of EM radiation measurements obtained over a predetermined length of time.

In some cases, each averaged single beam measurement of the plurality of Single Beam measurements is assigned a measurement frame.

In some cases, the second set of SB measurements comprises single beam measurements included in the first set of SB measurements.

In some cases, a portion of the SB measurements of the moving average sample SB value are included in the moving average background SB value.

In some cases, the method further comprises:
determining a ratio between the moving average sample SB value and the moving average background SB value;
determining a moving average differential Double Beam, which is in some cases the logarithmic of the ratio of the moving average sample SB value and the moving average background SB value;

In some cases, the number of frames included of SB measurements of the set of the average sample SB alternate between predetermined values. In some cases, the number of frames SB measurements of the set of the average background alternate between predetermined values.

It is another object of the subject matter to disclose a system for detecting concentration of air contaminants comprises:

an open path instrument enabled to collect intensity measurements of EM radiation;

at least one processor enabled to convert the EM radiation measurements into an absolute concentration quantity;

a memory unit enabled to store the information obtained by the spectrometer and the processor.

a display enabled to display the results obtained by the processor.

In some cases, the system further comprises a display device for displaying results obtained by the processor.

In some cases, the processor comprises a SB unit for designating the SB measurement; a measurement frame unit for designating a measurement frame to the SB measurement; a moving average sample SB unit for determining the moving average sample SB value; a moving average background unit for determining the moving average background SB value; a DB unit for determining the moving average differential DB value; a moving average differential concentration unit for determining the moving average differential concentration.

In some cases, the spectrometer is an active open path spectrometer or a passive open path spectrometer. In some cases, the active open path spectrometer comprises an EM radiation source. In some cases, the spectrometer is a Fourier-transform infrared (FTIR).

BRIEF DESCRIPTION OF THE DRAWINGS

Exemplary non-limited embodiments of the disclosed subject matter will be described, with reference to the following description of the embodiments, in conjunction with the figures. The figures are generally not shown to scale and any sizes are only meant to be exemplary and not necessarily limiting. Corresponding or like elements are optionally designated by the same numerals or letters.

DETAILED DESCRIPTION

Figure 1:
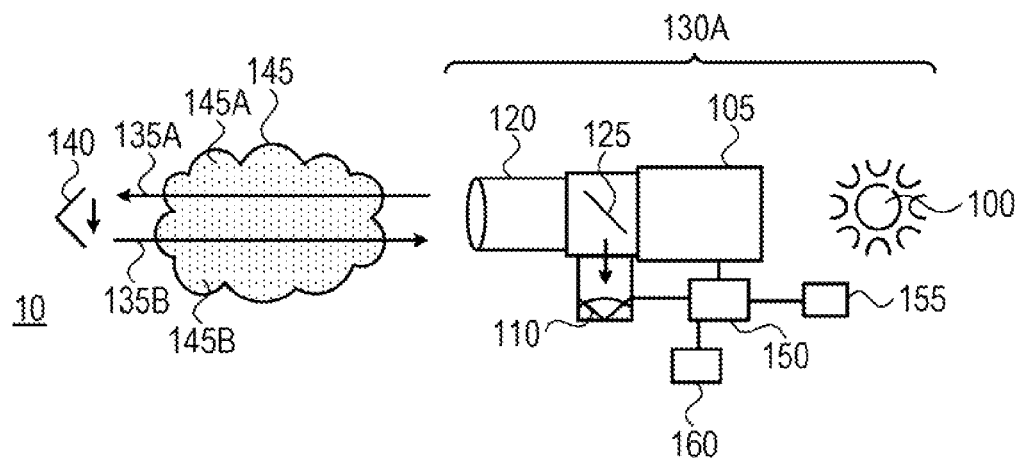
FIG. 1 shows an active, modulated monostatic Optical Remote Sensing (ORS) system suitable for use with the presently disclosed subject matter, according to some exemplary embodiment of the subject matter.
Figure 1:

The subject matter discloses a method and system for obtaining a concentration level of an air contaminant in a particular location. The method comprises obtaining Single Beam ("SB") measurements recorded frequently. The SB measurement comprises measured EM radiation value or spectral data. In some exemplary embodiments, the SB measurement is a time averaged value of a plurality of measured EM radiation measurements recorded over a predetermined time period, for example, EM radiation measurements recorded over 30 seconds. The SB measurement may be obtained in a continuous manner or in predetermined intervals, for example, a SB measurement is recorded every 5 minutes at a specific location over a predetermined period of time. The recorded SB measurement is assigned a measurement frame, which is an index number that counts the number of SB measurements recorded over a given path. The path can be open path or extractive.

After the SB measurements are recorded, an average sample SB value is determined for a chosen set of SB measurement. In some exemplary embodiments the SB value may be a multi-wavelength spectrum, such as Fourier Transform Infra-Red measurements. The average sample SB value is obtained over a sequence of frames of SB measurements, which maps over the original SB measurements. As an updated frame of SB measurement is recorded, the recorded SB measurement is added to the updated average sample SB value and the SB measurement with the smallest index frame number is removed from the SB measurements that assemble the updated average sample SB value, to generate a series of moving average sample SB values. For example, if the latest average sample SB value is comprised from frames 9-11, when frame 12 is recorded the updated average sample SB is comprised from frames 10-12. A moving average sample SB value is compared with the moving average background SB value in order to determine a moving average differential Double Beam ("DB") value. The DB value is used to evaluate the quantity of the air contaminant. The DB may be used to determine the concentration using transmission, absorption, emission or extinction, or any value that compares the sample SB value with the corresponding background SB value. The moving average background SB value is obtained by averaging SB measurements with smaller index frames than the measurement frames of the moving average sample SB measurement for which the moving average differential DB is being determined. In some exemplary embodiments, the moving average sample SB value and the moving average background SB value may have overlapping measurement frames. For example, the average sample SB value may comprise of SB measurements with designated measurement frames 12-20 and the average background SB value may comprise of SB measurements with designated measurement frames 11-19. In some cases, the moving average differential DB is determined by taking a logarithmic value of the average sample SB value divided by the average background SB value. The moving average differential DB value is used to determine a moving average differential concentration, which is consequently used to determine an absolute concentration of the air contaminant. In some exemplary embodiments of the subject matter, an average differential emission value is determined rather than the average differential absorption value for determining the differential concentration of the air contaminant.

In some exemplary embodiments of the subject matter a moving average sample SB value is obtained, rather than the average sample SB value. The SB measurements are obtained in a continuous manner, which continuously updates the sample spectrum with the new SB measurements. The value of the moving average sample SB value is updated to a new value every time a new SB measurement is collected. The moving average sample SB value comprises SB measurements that overlap with a prior moving average sample SB value. In the exemplary embodiments, a moving average background SB value is also determined in the same manner as the moving average sample SB value. The moving average background SB value comprises SB measurements that overlap with a prior moving average background SB value. A moving average differential DB is determined by comparing the moving average sample SB value and the moving average background SB value. The methods explained hereinafter may be implemented with a moving average differential average in the same manner it is implemented for the average differential DB for determining the differential concentration.

There are three data acquisition scenarios. The first discloses a series of EM spectra or values $S(\lambda)$ (intensity S vs. wavelength $\lambda$ or intensity at a specific wavelength) acquired sequentially over a defined path length (extractive or open path). The second discloses a series of EM spectra or values acquired sequentially over a spatially adjacent direction. This can be achieved for example with passive infrared or ultraviolet on the sky or to a blocking mountain range. The third scenario discloses a series of EM spectra or values acquired sequentially over the same direction from a moving platform. Examples: solar occultation flux, mobile sky looking spectroscopy, and airborne down looking spectroscopy.

FIG. 1 shows an active modulated optical remote sensing (ORS) system for estimating a maximum concentration of an air contaminant, according to exemplary embodiments of the subject matter. The active modulated ORS system comprises an EM radiation source 100, wavelength separator 105, and a detector 110 all positioned at the same end of a monitoring path 115. In this exemplary configuration, a transmitting/receiving optics 120 and beamsplitter 125 are also positioned at the same end of the monitoring path 115. A spectrometer module 130A comprises the EM radiation source 100, the wavelength separator 105, the detector 110, the transmitting/receiving optics 120, and the beamsplitter 125. In some exemplary embodiments, the transmitting/receiving optics 120 may be selected from a group consisting of a Cassegrain telescope and a Newtonian telescope. The active modulated ORS system comprises an ORS system 20 that comprises an instrument adapted for emitting energy along the monitoring path 115, wherein the radiation from the EM radiation source 100 is emitted along the monitoring path 115, which is defined by a first end point 115A, and a second end point 115B, of a line of measurement.

In some exemplary embodiments, the EM radiation source 100 may comprise a broadband infrared energy source, for example a globar, i.e., a silicon carbide rod, and an incandescent wire comprising nichrome or rhodium sealed in a ceramic cylinder. In this exemplary embodiment, the energy emitted by the EM radiation source 100 is modulated, for example, by an interferometer, which may comprise the wavelength separator 105. In some exemplary embodiments, the energy source may comprise a tunable diode laser, for example a tunable diode laser operating in the near-infrared spectral region. In some exemplary embodiments, the energy source may comprise a UV bulb as the EM radiation source in the active open path device.

The detector 110 detects the radiation emitted by the EM radiation source 100 and produces a signal that is indicative of one of a path-integrated concentration, and a path-averaged concentration of one or more of target species 145A and 145B, which comprise a plume 145 along the path 115. It is noted that the target species 145A and 145B are exemplary and provided for illustration only.

In some exemplary embodiments, the detector 110 may comprise a thermal detector, such as a pyroelectric deuterated triglycine sulfate (DTGS), which operates at room temperature. Another exemplary embodiment, the detector may comprise a photo-conducting detector, for example, a mercury-cadmium-telluride (MCT) detector, which operates at temperature much below room temperature.

The detection range of the detector 110 should be matched to a spectral range of radiation emitted by EM radiation source 100. Accordingly, in some exemplary embodiments, the ORS system 20 may comprise the EM radiation source 100, the detector 105, and other optical components, such as reflectors 140, beamsplitters 125, and the like, which are designed to operate in the mid-infrared spectral range (e.g., approximately a 2-.mu.m to 20-.mu.m (about 5000-cm-.sup.−1 to about 500-cm.sup.−1 spectral range).

In exemplary embodiments wherein the presently disclosed ORS system comprises a tunable diode laser, the tunable diode laser can operate in the 0.6- to 2.0-.mu.m wavelength region, and in some exemplary embodiments, in the 1.4- to 1.8-.mu.m wavelength region.

The transmitting/receiving optics 120 is used to transmit and receive an optical beam, separated to into a transmitted optical beam 135A and a received optical beam 135B, along the monitoring path 115. To transmit and receive the optical beams 135A and 135B with the same transmitting/receiving optics 120, the beamsplitter 125 is positioned to divert part of the received optical beam 135*b* to the detector 110. In this exemplary configuration, the transmitted optical beam 135*a* and the received optical beam 135*b*, traverse the beamsplitter 125 twice.

The reflectors 140 are positioned at the opposite end 15B of the monitoring path 115 from the transmitting/receiving optics 120. In some exemplary embodiments, the retroflector 140 may comprise a single reflecting element, for example, a corner-cube retroflector array, which returns the received optical beam 135B substantially along the same direction from which it was transmitted.

The energy, for example a mid-infrared or near-infrared radiation, is emitted from the EM radiation source 100 and directed though the wavelength separator 105, for example, through an interferometer, where the energy is modulated at a predetermined frequency. The modulated energy exits the wavelength separator 105 and is collimated by the transmitting/receiving optics 120 before it is transmitted along the monitoring path 115, where it interrogates the plume 145. The transmitted optical beam 135A is redirected back towards reflecting element 140 along the monitoring path 115. The reflecting element 140 reflects the received optical beam 135B, which returns on the substantially the same monitoring path 115 as the transmitted optical beam 135A. The received optical beam 135B is collected by the transmitting/receiving optics 120 and directed to the detector 110 by the beamsplitter 125. The detector 110 records a signal that is indicative of the apparent absorbance spectrum of gases, vapors, aerosols, and particles, which is further indicative of one of a path-integrated concentration and a path-averaged concentration of one or more air contaminants. The detector 110 is connected to a processor 150, which may connected to a memory 155, in which a plurality of machine instructions and/or data may be stored. The processor 150 may be connected to a display/printer 160, which provides a display of the data.

In some exemplary embodiments of the subject matter, the system 10 may comprise an open-path Fourier transform infrared system, in which the energy emitted from the energy source 100 is modulated by the wavelength separator 105. In this exemplary embodiment the processor 150 may be instructed to accept only the modulated radiation from the energy source 100 and to reject unmodulated ambient radiation. Such a configuration allows the cancellation of environment radiation that could introduce noise and error to the measurement due to atmospheric temperature scintillation effects. Further, because the detector 110 and wavelength separator 105 are at the same end of the monitoring path 115, the monitoring path 115 is not limited by any communications requirements between the detector 110 and the wavelength separator 105. For example, open-path Fourier transform infrared monitors in a monostatic configuration can achieve a monitoring path-length of about 500 meters (optical path-length of 1,000 meters).

Figure 2:
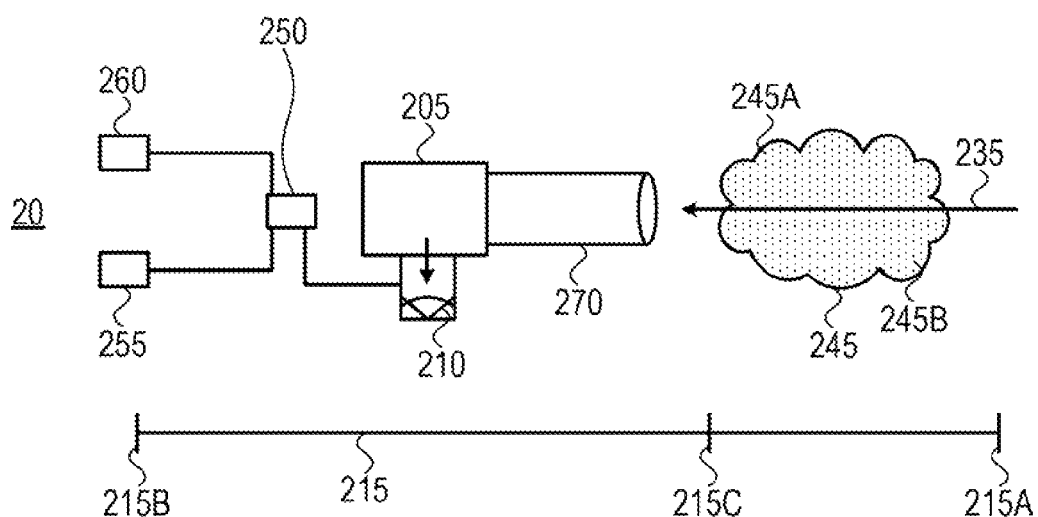
FIG. 2 shows a passive ORS system in which the ambient environment in the field of view of the receiving optics supplies the radiation, which interrogates the plume, according to some exemplary embodiment of the subject matter.

FIG. 2 shows a passive ORS infrared system 20, according to exemplary embodiments of the subject matter. The passive optical remote infrared system 20 relies on ambient environment radiation, which is emitted from natural surfaces that are only a few degrees different in temperature from the absorbing or emitting medium as the energy source. The passive ORS infrared system 20 comprises a receiving optics 270, the wavelength separator 205, and the detector 210. In an exemplary embodiment of the subject matter, the temperature of the plume 245 must be higher than that of the ambient environment in the view of the receiving optics 270 in order for the receiving optics 270 to collect emission lines from the plume 245. If the temperature of the ambient environment behind the plume is higher than the temperature of the plume 245, the air contaminants comprising the plume 245 attenuate the ambient environment radiation and produce absorption lines. If the temperature of the ambient environment behind the plume 245 is lower than the temperature of the plume 245, the air contaminants comprising the plume 245 emit radiation in addition to the ambient environment radiation and produce emission lines.

After the ambient radiation interrogates the plume 245, the radiation is detected by the detector 210. The detector 210 is connected to the processor 250. The processor 250 is connected to the memory 255, in which a plurality of machine instructions and data recorded by the passive ORS system are stored. The processor 250 may also be connected to the display 260, which displays the data collected.

Figure 3:
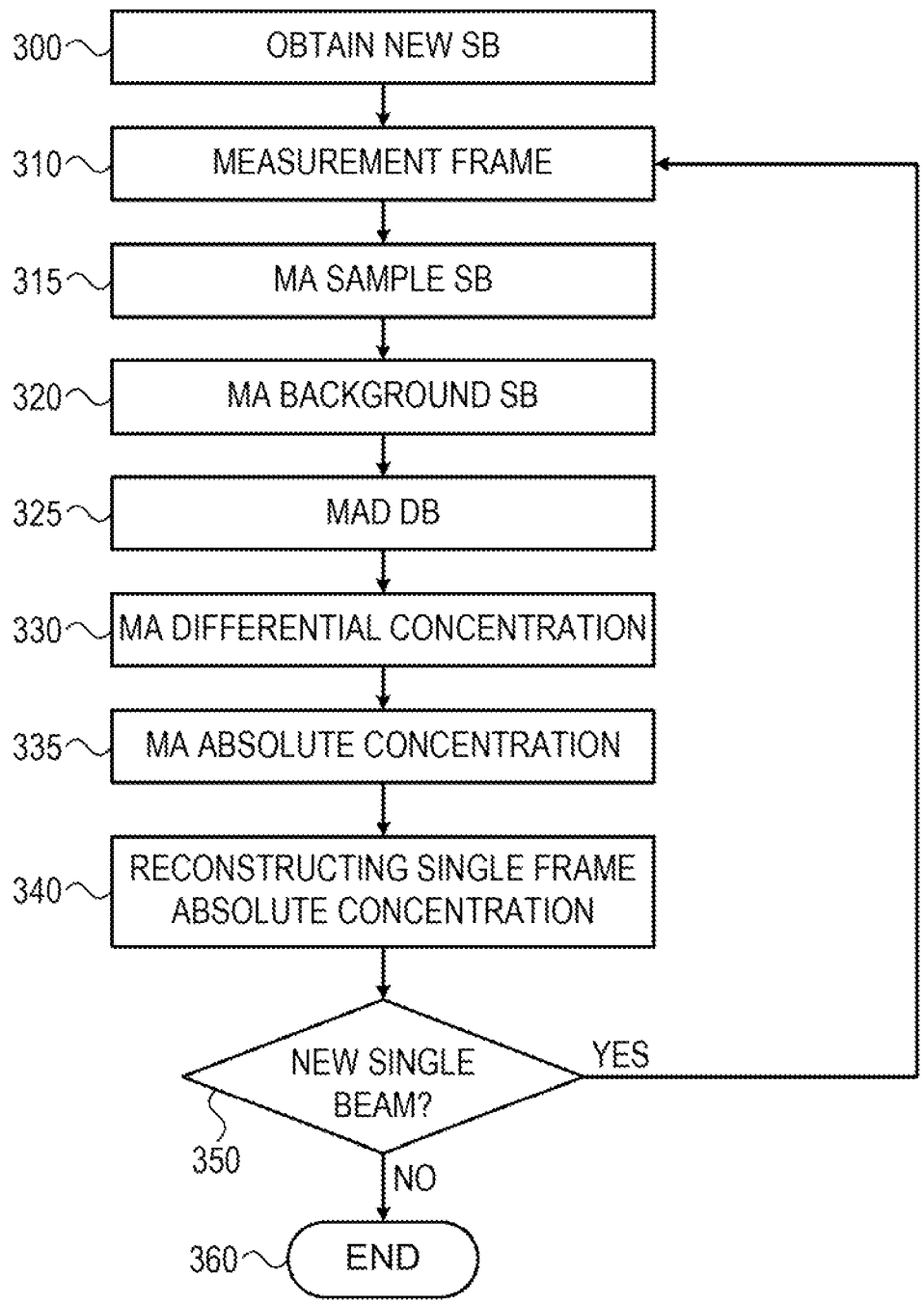
FIG. 3 shows a method for detecting the concentration of air contaminants, according to some exemplary embodiment of the subject matter.

FIG. 3 shows a method for determining a concentration level of an air contaminant, according to exemplary embodiment of the subject matter. In step 300, the system obtaining a new SB measurement. The new SB measurement may comprise of averaged EM radiation measurements recorded over a predetermined time period, for example 30 seconds or 1 minute. The new SB measurement is collected by a detector, for example the detector 110 in FIG. 1, and is then transferred to a processor, such as the processor 150 of FIG. 1. Multiple SB measurements may be collected over a length of time, each of the SB measurements may comprise averaged EM radiation measurements. The multiple SB measurements may be collected either continuously or at predetermined intervals, for example every 5 minutes over a given path length.

Step 310 discloses assigning a measurement frame to the collected SB measurement. The measurement frame is an index number that counts the number of SB measurements that are measured over a given path. The measurement frame may be assigned in a continuous format or in predetermined intervals. For example, the 120$^{th}$ SB measurement obtained by the detector 110 from FIG. 1 is assigned by the processor 150 the measurement frame of 120, while the following measurement, the 121$^{st}$ SB measurement, is assigned the measurement frame of 121.

Step 315 discloses determining a moving average (MA) sample SB value. The MA sample SB value is determined by averaging SB measurements over a predetermined averaging coefficient. The SB measurement frames averaged to determine the MA sample SB value are defined as a first set of SB measurements. The predetermined averaging coefficient is a number of sequential SB measurements the processor 150 assigns for determining the MA sample SB value. For example, the MA sample SB value is determined for a SB measurement with measurement frame 12, the predetermined averaging coefficient is 3, the processor 150 designates the SB with measurement frame 12 and the preceding two SB measurements to be averaged. Hence, the processor 150 determines the MA sample SB value by taking the average of the SB measurements with the measurement frames 10, 11, and 12. In this case, the first set of SB measurements comprises measurement frames 10, 11, and 12.

Step 320 discloses determining a MA background SB value. The MA background SB value is determined by averaging SB measurements over a predetermined averaging coefficient. The single beam measurements averaged to determine the MA background SB value are defined as a second set of SB measurements. The second set of SB measurements comprises a plurality of SB measurements recorded prior to the SB measurements of the first set of SB measurements. The SB measurements of the second set are chosen by an offset parameter, which dictates which prior SB measurements are used for the MA background SB value. The averaging coefficient for the MA background SB value may be equal to the averaging coefficient of the average sample SB value. In some exemplary embodiments, the MA sample SB value and the MA background SB value may comprise overlapping measurement frames. The overlapping measurement frames are defined by having the same SB measurement in both the first set of SB measurements and the second set of SB measurements. For example, the MA sample SB value comprises an average of 3 SB measurements with measurement frames 10, 11, and 12. If the offset parameter is 1, the MA background SB value comprises the averaged value of the SB measurements with measurement frames, 9, 10, and 11.

Step 325 discloses determining a moving average differential (MAD) DB value. In some case, the MAD DB value is an absorbance spectrum which is the negative logarithmic ratio of the MA sample spectrum divided by the MA background SB value, also shown in the formula below, having an offset of a single frame:

$$A_n^{MAD_m}(v) = -\log_{10}\left\{\frac{[S_n(v) + S_{n-1}(v) + \ldots S_{n-m+1}(v)]/m}{[S_{n-1}(v) + S_{n-2}(v) + \ldots S_{n-m}(v)]/m}\right\}$$

Wherein $A_n^{MAD_m}(v)$ defines the MAD absorbance value, m defines the averaging coefficients for both the MA background value and the MA sample SB value, the numerator defines the first set of SB measurements and the denominator defines the second set of SB measurements. n denotes the latest frame index.

The MAD DB value allows for determining the MA differential concentration of the air contaminant. The MAD DB value represents the MAD value of EM radiation absorbed or emitted by the air contaminant.

Step 330 discloses determining an MA differential concentration value. The MA differential concentration value is determined by comparing the value of radiation emitted or absorbed in the MAD DB value with a predefined reference emission or absorption radiation value given in a predetermined quantity and path length. The predefined reference emission or absorption radiation value may be theoretical or empirical.

Step 335 discloses determining the MA absolute concentration value. The absolute concentration value is stored in the memory 160. Determination of the MA absolute concentration value may be determined by integrating the MA differential concentration over time.

Step 340 discloses reconstructing the single frame absolute concentration. Simple algebraic manipulation of the DB equation above allows the reconstruction of the contribution of the latest frame absolute concentration to the current MA absolute concentration.

Step 350 discloses detecting whether a new SB measurement is recorded by the detector 110. If the detector 110 has recorded a new SB measurement, the processor 150 returns to step 310 with the new SB measurement.

The processor 150 in FIG. 1 receives new SB measurements, which the processor 150 designates to be part of the first set of SB measurements that assemble a new average sample SB value. In some exemplary embodiments of the subject matter, the new average sample SB value may comprise overlapping SB measurements of the previous average sample SB value along with the new SB measurements. For example, while the previous average sample SB value comprises SB measurements with measurement frames 2-6; the new average SB value may comprise SB measurements with measurements 5-9. The overlap between the previous average sample SB value and the new average sample SB value occurs on the SB measurements with measurements frames 5 and 6, and the new average sample SB value have the measurement frames 7-9. In some exemplary embodiments of the subject matter, there is no overlapping between the previous average sample SB value and the new average sample SB value. For example, the previous averaged sample SB value comprises SB measurements with measurement frames 3-7; however, the new averaged sample SB value comprises the new SB measurements with measurement frames 8-12.

After the collection of new SB measurements, a new average background SB value is designated. In some exemplary embodiments of the subject matter, the new average background SB value may comprise overlapping measurements of the previous average background SB value. For example, the previous average background SB value comprises SB measurements with measurement frames 1-5; the new average background SB value may comprise SB measurements with measurements 3-7. The overlap between the average background SB value and the new average background SB value occurs on the SB measurements with measurements frames 3-5. In some exemplary embodiments of the subject matter, there is no overlapping between the average background SB value and the new average background SB value. For example, the previous averaged background SB value comprises SB measurements with measurement frames 1-5; however, the new averaged background SB value comprises the new SB measurements with measurement frames 6-9.

If no new SB measurement has been recorded by the detector, 110, then step 360 is performed. In step 360, no new SB measurement has been recorded by the detector 110, and the processor ceases from repeating the method.

Figure 4:
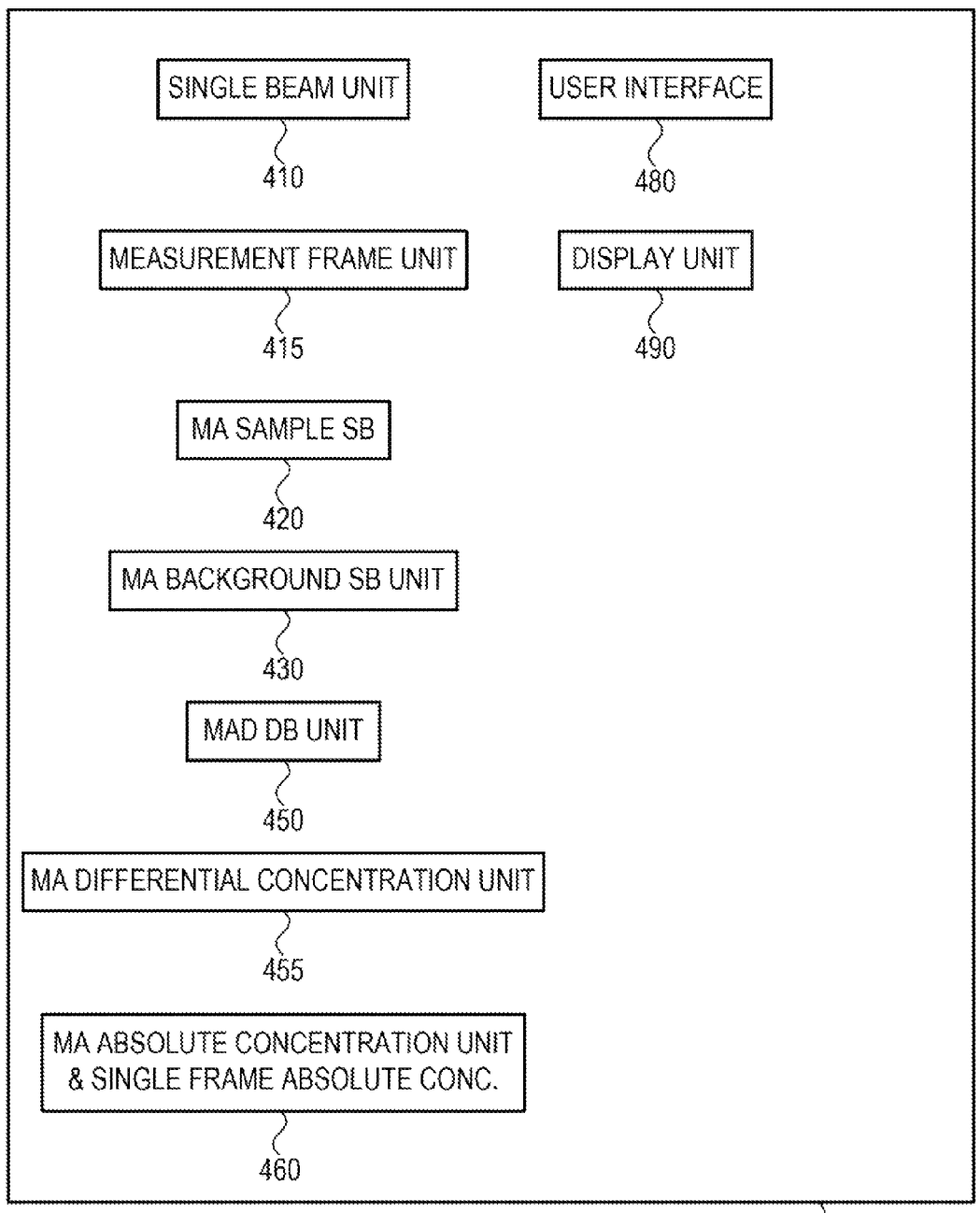
FIG. 4 shows a system for detecting the concentration of air contaminants, according to some exemplary embodiment of the subject matter; and, FIG. 5 shows a plot of a differential moving average concentration and a plot of both the absolute moving average concentration and reconstructed frame concentration, according to some exemplary embodiment of the subject matter.

FIG. 4 shows a system for detecting concentration level of air contaminants, according to exemplary embodiments of the disclosed subject matter. The system 400 comprises a single beam unit 410 (SB unit), which records the SB measurements obtained by the detector 110. In some exemplary embodiments, the SB unit 410 records a plurality of EM radiation measurements over a predetermined length of time, for example 30 seconds. The SB unit 410 averages the EM radiation measurements and designates the output as the SB measurement. The processor 150 then transmits the SB measurement to a measurement frame unit 415, which designates a measurement frame for the SB measurement.

The system 400 comprises a moving average sample SB unit 420, which calculates the average sample SB value. The moving average sample SB value 420 designates the measurement frame for which the average sample SB value is being obtained. The moving average sample SB unit 420 obtains the predetermined averaging coefficient, which is used to determine the number of measurement frames that are used to calculate the average sample SB value. In some exemplary embodiments, the predetermined averaging coefficient is entered by a user of the ORS system 20 of FIG. 2 through a user interface 480.

The system 400 comprises a moving average background SB unit 430. The moving average background SB unit 430 designates the SB measurements that are used to calculate the average background SB value. The moving average background SB unit 430 obtains the offset parameter, for example from the user interface 480. The offset parameter is the difference between a first measurement frame used to determine the average background SB value and a first measurement frame used to determine the average sample SB value.

The system 400 may also comprise a MAD DB unit 450 that determines the MAD DB value by taking, for example, the negative logarithmic value of the average sample SB value divided by the average background SB value. The MAD DB value is transferred to a MAD concentration unit 455, which determines the MAD concentration value. The MAD concentration value is transferred to a MA absolute concentration unit 460. The MA absolute concentration unit 460 obtains the MA absolute concentration of the of the air contaminant by integrating the MAD concentration values. The MA absolute concentration unit 460 may be used for reconstructing the single frame absolute concentration. Simple algebraic manipulation of the DB equation above allows the reconstruction of the contribution of the latest frame absolute concentration to the current MA absolute concentration.

A display unit 490 transfers the data received to either a computerized display or a printer that will display the concentration of the air contaminant. In some exemplary embodiments the display of the information is on a timed plot, in which the x-axis is time and the y-axis is concentration in parts per million (ppm) or parts per billion (ppb).

Figure 5:
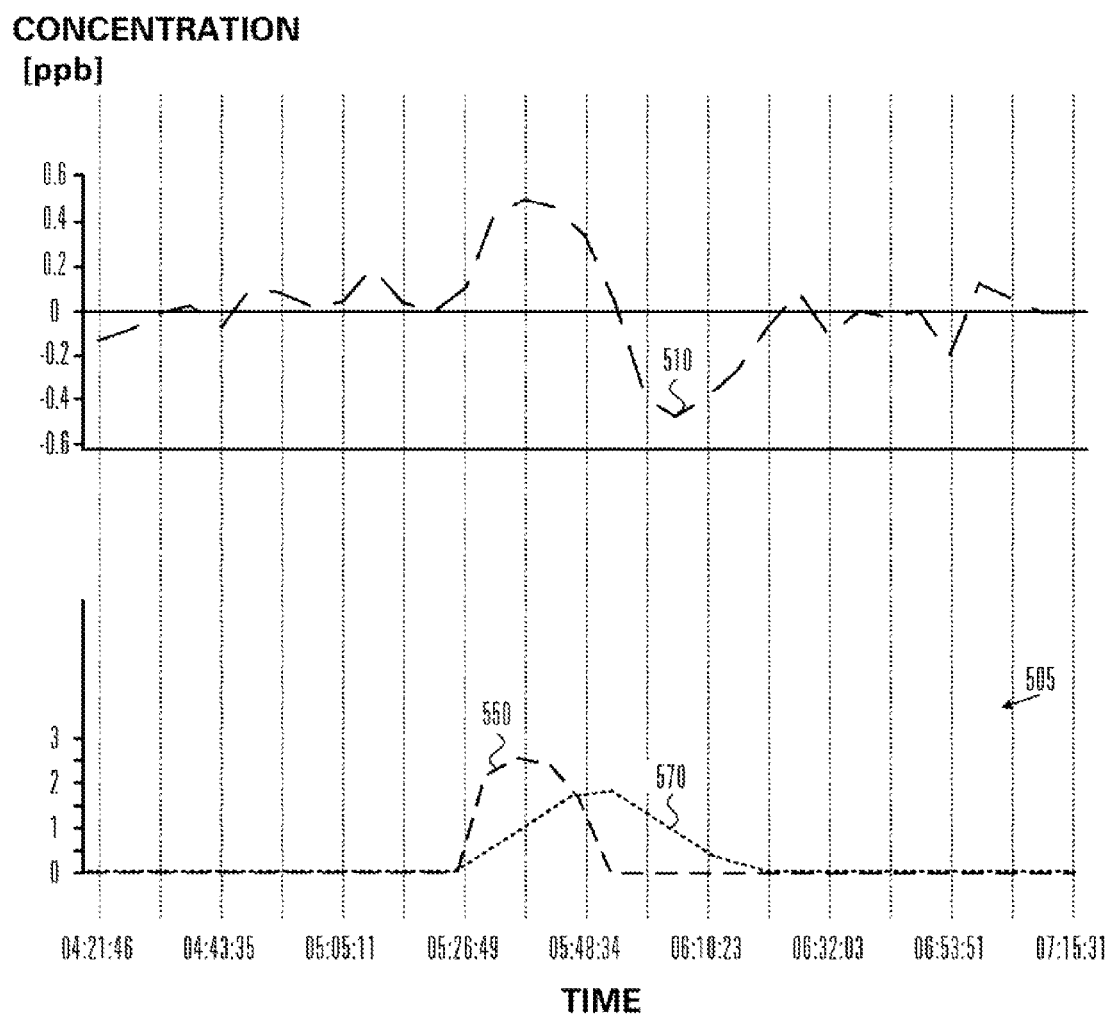

FIG. 5 shows a plot for the moving average differential concentration 500 and plots for absolute concentration 505, according to exemplary embodiment of the subject matter. The plot for the differential concentration 500 shows a raw MAD concentration plot 510 obtained by the processor 150.

The plot 505 comprises of an integrated moving average absolute concentration 570, which displays the concentration of the air contaminant as the integration of the raw MAD concentration in plot 510. The plot for absolute concentration 505 shows the plot of a reconstructed single frame absolute concentration 550, which is generated by reconstructing the single frame absolute concentration. Simple algebraic manipulation of the DB equation above allows for direct reconstruction of the contribution of the latest frame absolute concentration to the current MA absolute concentration.

The plots for absolute concentration 505 can be generated in another process. The determined concentration EM contributions to the current average background SB value or spectrum for all detected compounds, are subtracted prior to generation of the DB value. In this case, the DB value is not differential and this DB produces directly moving average absolute concentrations shown in plot 570 that discloses integrated moving average absolute concentration and consequently in the same manner the single frame absolute concentration shown in plot 550.

While the disclosure has been described with reference to exemplary embodiments, it will be understood by those skilled in the art that various changes may be made and equivalents may be substituted for elements thereof without departing from the scope of the subject matter. In addition, many modifications may be made to adapt a particular situation or material to the teachings without departing from the essential scope thereof. Therefore, it is intended that the disclosed subject matter not be limited to the particular embodiment disclosed as the best mode contemplated for carrying out this subject matter, but only by the claims that follow.

The invention claimed is:

1. A method for detecting concentration of air contaminants, comprising:
    obtaining an average sample single beam value, the average sample single beam value comprises a first set of single beam measurements obtained from a detector,
    obtaining an average background single beam value, the average background single beam value comprises a second set of single beam measurements obtained from the detector,
    comparing the average sample single beam value to the average background single beam value to determine the concentration of air contamination;

continuously updating the average sample single beam value and the average background single beam value upon detection of new single beam measurements;

wherein the second set of single beam measurements comprises a plurality of single beam measurements that were detected by the detector prior to the detection of the single beam measurements included in the first set of single beam measurements.

2. The method of claim 1, wherein each single beam measurement of the plurality of single beam measurements comprises an electromagnetic radiation measurement.

3. The method of claim 2, wherein the electromagnetic radiation measurement comprises an average of a plurality of electromagnetic radiation measurements obtained over a predetermined length of time.

4. The method of claim 1, wherein each single beam measurement of the plurality of single beam measurements is assigned a measurement frame.

5. The method of claim 1, wherein a portion of the single beam measurements of the average sample single beam value are included in the average background single beam value.

6. The method of claim 1, further comprises:
determining an average differential double beam by calculating a ratio between the average sample single beam value and the average background single beam value;
calculating a logarithm of the ratio of the average sample single beam value and the average background single beam value;
determining an average differential concentration value by comparing the value of radiation emitted or absorbed in the average differential double beam value with a predefined reference emission or absorption radiation value given in a predetermined quantity and path length;
determining an average absolute concentration by integrating over time the average differential concentration.

7. The method of claim 1, wherein the number of single beam measurements of the first set of the average sample single beam value alternates between predetermined values.

8. The method of claim 1, wherein the number of single beam measurements of the second set of the average background single beam value alternates between predetermined values.

9. The method of claim 1, wherein:
the average sample single beam value is a moving average sample single beam value, the moving average sample single beam value comprises single beam measurements that overlap with a prior moving average sample single beam value;
the average background single beam value is a moving average background Single Beam value, the moving average background single beam value comprises single beam measurements that overlap with a prior moving average background single beam value.

10. The method of claim 9, further comprising:
determining a moving average differential double beam by calculating a ratio between the moving average sample single beam value and the moving average background single beam value;
calculating a logarithm of the ratio of the moving average sample single beam value and the moving average background single beam value;
determining a moving average differential concentration by comparing the value of radiation emitted or absorbed in the moving average differential double beam value with a predefined reference emission or absorption radiation value given in a predetermined quantity and path length;
determining a moving average absolute concentration by integrating over time the moving average differential concentration.

11. A system for detecting concentration of air contaminants comprises:
an instrument enabled to collect measurements of electromagnetic radiation;
an at least one processor enabled to convert the electromagnetic radiation measurements into an absolute concentration quantity; wherein the at least one processor comprises:
a single beam unit for designating the single beam measurement;
a measurement frame unit for designating a measurement frame to the single beam measurement;
a moving average sample single beam unit for determining the moving average sample single beam value;
a moving average background single beam unit for determining the moving average background single beam value;
a double beam unit for determining the moving average differential double beam;
a moving average differential concentration unit for determining the moving average differential concentration;
an absolute concentration unit for determining an absolute concentration;
a memory unit enabled to store the information obtained by the instrument and the processor;
a display device enabled to display the results obtained by the processor.

12. The system of claim 11, wherein the instrument is an extractive spectrometer, an active open path spectrometer, or a passive open path spectrometer.

13. The system of claim 12, wherein the active open path spectrometer comprises an EM radiation source.

14. The system of claim 11, wherein the instrument is a Fourier-transform interferometer.

* * * * *